United States Patent [19]

Cordi et al.

[11] Patent Number: 5,278,191

[45] Date of Patent: Jan. 11, 1994

[54] DIPHENYLMETHYLAMINOACETAMIDE DERIVATIVES AS ANTI-CONVULSANTS

[75] Inventors: Alexis A. Cordi, St. Louis, Mo.; Claude L. Gillet, Blanmont, Belgium

[73] Assignee: G. D. Searle & Co., Chicago, Ill.

[21] Appl. No.: 776,530

[22] Filed: Oct. 11, 1991

Related U.S. Application Data

[63] Continuation of Ser. No. 239,086, Aug. 31, 1988, abandoned.

[51] Int. Cl.⁵ .................. A61K 31/165; C07C 237/20
[52] U.S. Cl. ................................ 514/620; 514/227.5;
514/237.5; 514/255; 514/423; 514/618;
544/58.4; 544/162; 544/391; 546/226; 548/540;
564/162; 564/164; 564/165
[58] Field of Search .................. 564/162, 165, 164;
514/618, 620, 226

[56] References Cited

U.S. PATENT DOCUMENTS

| 3,821,249 | 6/1974 | Malen et al. | 424/320 |
| 4,025,651 | 5/1977 | Kirino et al. | 424/320 |
| 4,400,394 | 8/1983 | Kaplan et al. | 514/620 |
| 4,639,468 | 1/1987 | Ronucci et al. | 514/620 |

FOREIGN PATENT DOCUMENTS

| 636245 | 8/1963 | Belgium . | |
| 706262 | 11/1967 | Belgium . | |
| 1181673 | 4/1967 | United Kingdom . | |
| 2063867 | 6/1981 | United Kingdom | 564/164 |

OTHER PUBLICATIONS

R. M. Peck et al., *J. Med. Chem*, 19(12), pp. 1422-1423 (1976).
A. G. de Vazquez et al., *Anales Assoc. Quim Argentina*, 60, pp. 501-507 (1972).
B. Wysocka-Skrzela, *Pol. J. Chem*, 56 (10-12), 1573-1576 (1982).
E. C. Taylor et al., *J. Am. Chem. Soc*, 103, pp. 7743-7752 (1981).

*Primary Examiner*—Richard L. Raymond
*Attorney, Agent, or Firm*—J. Timothy Keane; Joseph W. Bulock

[57] ABSTRACT

A class of diphenylmethylaminoacetamide derivatives is described having use in treatment of CNS dysfunctions such as epilepsy and convulsive disorders. Compounds of most interest are those of the formula

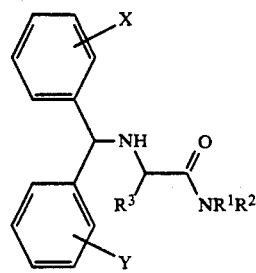

wherein each of X and Y is independently selected from hydrido and halo; and wherein each of $R^1$, $R^2$ and $R^3$ is hydrido; or a pharmaceutically-acceptable salt thereof.

5 Claims, No Drawings

DIPHENYLMETHYLAMINOACETAMIDE DERIVATIVES AS ANTI-CONVULSANTS

This is a continuation of application Ser. No. 07/239,086 filed Aug. 31, 1988, now abandoned.

FIELD OF THE INVENTION

This invention is in the field of clinical neurology and relates to a class of compounds, compositions and methods useful for treatment of Central Nervous System (CNS) dysfunctions. Of particular interest is a class of diphenylmethylaminoacetamide compounds for use as anti-convulsants and in management of epilepsy.

BACKGROUND OF THE INVENTION

Convulsive disturbances are typically observed in humans as rapidly alternating contractions and relaxations of muscles which are manifested by irregular movements of the limbs or body and typically accompanied by unconsciousness. The most common cause of convulsions in human adults is epilepsy. Convulsive seizures occur in children from a variety of causes. Convulsions in children may be due to brain damage from birth injuries, or due to dietary deficiencies such as a lack of vitamin D, or due to metabolic disorders such as hypoglycemia or hypokalemia, or due to a sudden body temperature elevation caused by infections such as pneumonia. Convulsions may also be initiated by brain diseases such as meningitis, encephalitis or tumors, and also by conditions brought on by asphyxia or skull fracture.

Acetamide derivatives have been investigated for various CNS uses. For example, Belgian Patent No. 706,262 describes a class of tricyclic compounds, namely, diphenylenemethane amine and amide derivatives, mentioned for use as anti-convulsants, as well as for anti-depressive, anti-inflammatory and analgesic uses. U.S. Pat. No. 3,821,249 describes another series of tricyclic-type dibenzothiazepin derivatives asserted to possess psychostimulant, anti-depressive, analgesic, anti-tussive, anti-histaminic and gastric anti-secretory properties. U. S. Pat. No. 4,639,468 describes a class of 2-amino-acetamide derivatives, having use in treatment of epilepsy, dyskinesia such as Parkinsonism, memory troubles and psychic disorders such as depression, with mention in particular of the compound diphenylpropylacetamide.

Various acetamide derivative compounds have been investigated for other pharmaceutical uses. For example, U.K. Patent No. 1,181,673 describes a series of tricyclic xanthen and thiaxanthen urea derivatives having utility in treatment of peptic ulceration. Carcinogenicity studies have been carried out involving a family of N-(9-acridinyl)glycylglycylglycine compounds [R.M. Peck et al, *J. Med. Chem.*, 19 (12), 1422-1423 (1976)]. A family of acridinylglycine derivatives has been reported to have tumor-inhibiting properties [B. Wysocka-Skrzela, *Pol. J. Chem.*, 56 (10-12), 1573-1576 (1982)]. Belgian Patent No. 636,245 describes a family of 2-(ω-alkoxycarbonylalkylideneamino)acetamides having pharmaceutical properties.

Diphenylmethylaminoacetic acid derivatives have been described as intermediates or end products of various laboratory-scale synthetic methods, without mention of pharmaceutical utility. For example, a series of N-benzhydrylaminoacetic acid compounds have been synthesized as intermediates for preparation of N-benzhydrylaminoacetic acid esters or derivatives, two such intermediates being 2-(diphenylmethylamino)acetamide and 2-[di-(para-methoxyphenyl)methylamino]acetamide [A. G. de Vazquez et al, *Anales Asoc. Quim. Argentina*, 60, 501-507 (1972)]. The compound α-diphenylmethylaminoacetamide was incidentally sythesized as a by-product in a multi-step preparation of a series of 3-oxo-1,2-diazetidinium ylides [E. C. Taylor et al, *J. Am. Chem. Soc.*, 103, 7743-7752 (1981)].

Other types of acetamide derivatives, such as glycinamide compounds, have been described for various purposes. For example, German Patent No. 2,511,311 describes a family of glycinamides for use as fungicides.

DESCRIPTION OF THE INVENTION

Treatment of a mammal afflicted with or susceptible to a CNS disorder, such as epilepsy, depression, convulsions, dyskinesia, cognitive disorder or other neurodegenerative disease or neurotoxic injury, is provided by administering to the mammal a therapeutically-effective amount of a compound selected from a class of diphenylmethylaminoacetamide compounds defined by Formula I:

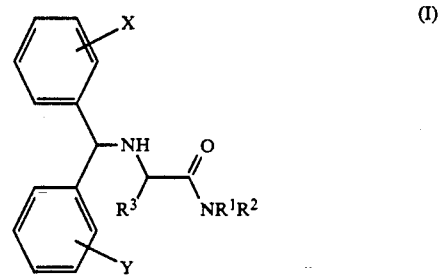

wherein each of X and Y is independently selected from hydrido, hydroxyl, alkyl, haloalkyl, halo, alkoxy, alkylthio, alkylsulfinyl, alkylsulfonyl, nitro, amino and alkylamino; wherein each of $R^1$ and $R^2$ may be hydrido or $R^1$ and $R^2$ may be taken together to form a heterocyclic group, so as to include the nitrogen atom which is attached to $R^1$ and $R^2$ of Formula I, said heterocyclic group selected from pyrrolidinyl, piperidinyl, piperazinyl, morpholino and thiomorpholino, any one of which heterocyclic groups may be substituted with one or more alkyl or aryl radicals; and wherein $R^3$ is hydrido or is a residue of a natural or an unnatural α-amino acid, said residue consisting of the fragment, other than hydrido, attached to the α-carbon of the α-amino acid; or a pharmaceutically-acceptable salt thereof.

It is believed that the compounds defined by Formula I are novel where the Formula I definition is qualified by the following proviso descriptions:

each of X, Y, $R^1$, $R^2$ and $R^3$ cannot be hydrido simultaneously; and when each of X and Y is para-methoxy, then at least one of $R^1$, $R^2$ and $R^3$ must be a group other than hydrido.

It is believed that novel pharmaceutical compositions, as well as novel methods of therapeutic treatment, are provided wherein a therapeutically-effective compound is selected, for inclusion in the composition or for use in the treatment, from the class of compounds defined by Formula I without qualification of Formula I with any of the foregoing proviso descriptions.

A preferred class of compounds within Formula I consists of those compounds wherein each of X and Y is independently selected from hydrido, hydroxyl, alkyl, haloalkyl, halo, alkoxy, amino and alkylamino; wherein each of $R^1$ and $R^2$ may be hydrido or $R^1$ and $R^2$ may be taken together to form a heterocyclic group including the nitrogen atom attached to $R^1$ and $R^2$ of Formula I, said heterocyclic group selected from pyrrolidinyl, piperidinyl, piperazinyl, morpholino and thiomorpholino, any one of which heterocyclic groups may be substituted with one or more of alkyl of one to about ten carbon atoms or phenyl; and wherein $R^3$ is hydrido or is a residue of a natural or an unnatural α-amino acid, said residue selected from alkyl, cycloalkyl, hydroxyalkyl, aminoalkyl, alkylthioalkyl, phenyl, phenylalkyl, hydroxybenzyl, cycloalkylalkyl, carboxyalkyl, mercaptoalkyl, carboxylalkylthioalkyl, diaminoalkyl, aminocarbonylalkyl, hydroxyhalophenylalkyl, aminohydroxyalkyl, heterocyclic, hydroxyheterocyclic, heterocyclicalkyl, aryloxyaralkyl and carboxyaminoalkylthioalkyl, any one of which $R^3$ groups having a substitutable position may be substituted with one or more groups selected from halo, hydroxy and alkyl; or a pharmaceutically-acceptable salt thereof.

A more preferred class of compounds within Formula I consists of those compounds wherein each of X and Y is independently selected from hydrido, hydroxyl, alkyl, haloalkyl, halo, alkoxy, amino and aminoalkyl, and wherein each of said alkyl-containing groups have one to about ten carbon atoms; wherein each of $R^1$ and $R^2$ is hydrido or $R^1$ and $R^2$ may be taken together to form a heterocyclic group including the nitrogen atom which is attached to $R^1$ and $R^2$ of Formula I, said heterocyclic group selected from pyrrolidinyl, piperidinyl, piperazinyl, morpholino and thiomorpholino, any one of which heterocyclic groups may be substituted with one or more groups selected from alkyl of one to about five carbon atoms and phenyl; and wherein $R^3$ is selected from hydrido, methyl, ethyl, isopropyl, hydroxymethylene, hydroxyethylene, n-butylene, isobutylene, aminobutylene, carboxymethylene, carboxyethylene, mercaptomethylene, carboxymethylaminodithiomethylene, methylthioethylene, phenyl, benzyl, para-hydroxylbenzyl, imidazolyl, imidazolylmethylene, 4-[4-hydroxy-3,5-diiodo-phenoxy]benzyl, indolyl, 3-indolylmethylene, 3-guanidinopropyl, carboxamidomethylene and carboxamidoethylene, any one of which $R^3$ groups having a substitutable position may be substituted with one or more groups selected from halo, hydroxy and alkyl; or a pharmaceutically-acceptable salt thereof.

A more highly preferred class of compounds within Formula I consists of those compounds wherein each of X and Y is independently selected from hydrido, hydroxyl, methyl, ethyl, n-propyl, isopropyl, n-butyl, sec-butyl, iso-butyl, n-pentyl, iso-pentyl, neopentyl, trifluoromethyl, halo, methoxy, ethoxy, propoxy, amino, aminomethylene, aminoethylene and aminopropylene; wherein each of $R^1$ and $R^2$ is hydrido or $R^1$ and $R^2$ may be taken together to form a heterocyclic group including the nitrogen atom which is attached to $R^1$ and $R^2$, said heterocyclic group selected from pyrrolidinyl, piperidinyl, piperazinyl, morpholino and thiomorpholino, any one of which may be substituted with one or more groups selected from methyl, ethyl, n-propyl, iso-propyl, n-butyl, iso-butyl, sec-butyl, tert-butyl, n-pentyl, iso-pentyl, neopentyl and phenyl; and wherein $R^3$ is hydrido or is a residue, other than hydrido, attached to the α-carbon of a natural or an unnatural α-amino acid, said amino acid selected from aspartic acid, asparagine, cystine, cysteine, glutamic acid, glutamine, glycine, histidine, δ-hydroxylysine, allo-δ-hydroxylysine, isoleucine, alloisoleucine, leucine, lysine, methionine, phenylalanine, serine, threonine, allo-threonine, tryptophan, tyrosine, dibromotyrosine, diiodotyrosine, valine, allylglycine, norvaline, norleucine, aminomalonic acid, aminoadipic acid, aminopimelic acid, pipecolinic acid, 5-hydroxypipecolinic acid, β-methyltryptophan, β-phenylserine, phenylglycine, cyclohexylglycine, cyclohexylalanine, furylalanine, thienylalanine, naphthylalanine and pyridylalanine; or a pharmaceutically-acceptable salt thereof.

A most highly preferred class of compounds within Formula I consists of those compounds wherein each of X and Y is independently selected from hydrido, fluoro and chloro; and wherein each of $R^1$, $R^2$ and $R^3$ is hydrido; or a pharmaceutically-acceptable salt thereof.

The term "hydrido" denotes a single hydrogen atom (H). The term "alkylene" embraces a methylene group, i.e., a —$CH_2$—group, or a series or chain of two or more methylene groups —$CH_2$—$(CH_2)_n$— wherein "n" is a whole number selected from two through about five, which chain is characterized in being divalent and containing no unsaturation, an example of which is an ethylene group (—$CH_2CH_2$—). Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to about ten carbon atoms, such as cyclopropyl, cyclobutyl, cyclohexyl and cycloheptyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy", embraces linear or branched oxy-containing radicals having an alkyl portion of one to about ten carbon atoms, such as methoxy, ethoxy, isopropoxy and butoxy. The term "alkylthio" embraces radicals containing a linear or branched alkyl group, of one to about ten carbon atoms, attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "sulfinyl" and "sulfonyl", whether used alone or linked to other terms, denote, respectively, the divalent radicals =SO and =$SO_2$. The term "heterocyclic" used alone or in conjunction with another term embraces ring structures having four to about nine ring members, one or two of which ring members being hetero atoms selected from oxygen, nitrogen and sulfur, and the remaining ring members being carbon atoms, which ring structure may be fully saturated, partially unsaturated or fully unsaturated, examples of such heterocyclic groups being imidazolyl, indolyl, pyrrolidinyl and thiomorpholino.

Within this class of diphenylmethylaminoacetamide compounds of the invention are the pharmaceutically-acceptable salts of the compounds of Formula I, including acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aralipathic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, alginic, $\beta$-hydroxybutyric, malonic, galactaric and galacturonic acid. Suitable pharmaceutically-acceptable base addition salts of compounds of Formula I include metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereomeric salts by treatment of the racemic mixture with an optically active acid or base. Examples of appropriate acids are tartaric, diacetyltartaric, dibenzoyltartaric, ditoluoyltartaric and camphorsulfonic acid. Then, the mixture of diastereomers maybe resolved by crystallization followed by liberation of the optically active bases from these salts. A different process for separation of optical isomers involves the use of a chiral chromatography column optimally chosen to maximize the separation of the enantiomers. Still another available method involves synthesis of covalent diastereomeric molecules by reacting compounds of Formula I with an optically pure acid in an activated form or an optically pure isocyanate. The synthesized diastereomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt. All of these stereoisomers, optical isomers, diastereomers, as well as mixtures thereof such as racemic mixtures, are within the scope of the invention.

GENERAL SYNTHETIC PROCEDURES

Compounds within Formula I can be synthesized in accordance with the following general procedures wherein for each formula shown the substitution pattern for X, Y, $R^1$, $R^2$ and $R^3$ is as defined before:

Reaction Scheme A

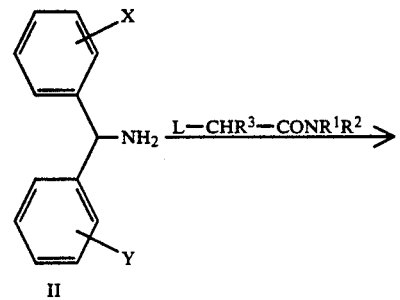

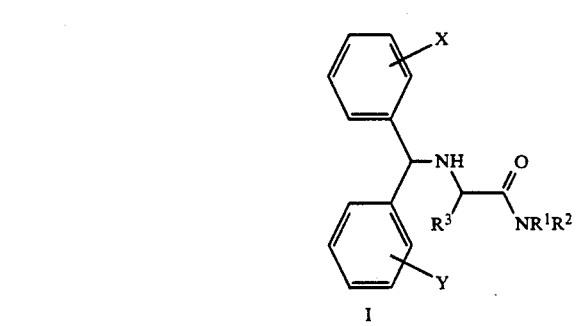

A first method which may be used to synthesize compounds of Formula I, as shown in Reaction Scheme A, involves reacting an amine of structure II with a reactant L—CHR$^3$—CONR$^1$R$^2$ wherein L is a good leaving group such as a halogen, a tosyl group, a mesityl group or equivalent. The reaction is best conducted in a solvent such as an alcohol, an ether or an amide (carboxamide or phosphoramide) at a temperature between about room temperature and reflux temperature of the selected solvent in the presence of a non-nucleophilic acid quencher such as a tertiary amine or a mineral base such as sodium bicarbonate.

Reaction Scheme B

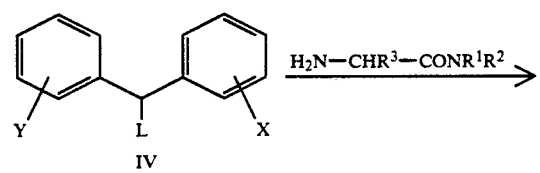

Reaction Scheme B (continued)

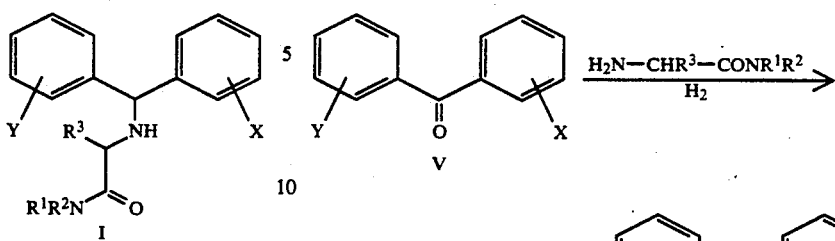

A second method which may be used to synthesize compounds of Formula I, as shown in Reaction Scheme B, involves reacting product of structure IV wherein L is a good leaving group such as a halogen, a tosyl group, a mesityl group or equivalent, with an amino amide derivative. The reaction is best conducted in a solvent such as an alcohol, an ether or an amide (carboxamide or phosphoramide) at a temperature between about room temperature and reflux temperature of the selected solvent in the presence of a non-nucleophilic acid quencher such as a tertiary amine or a mineral base such as sodium bicarbonate.

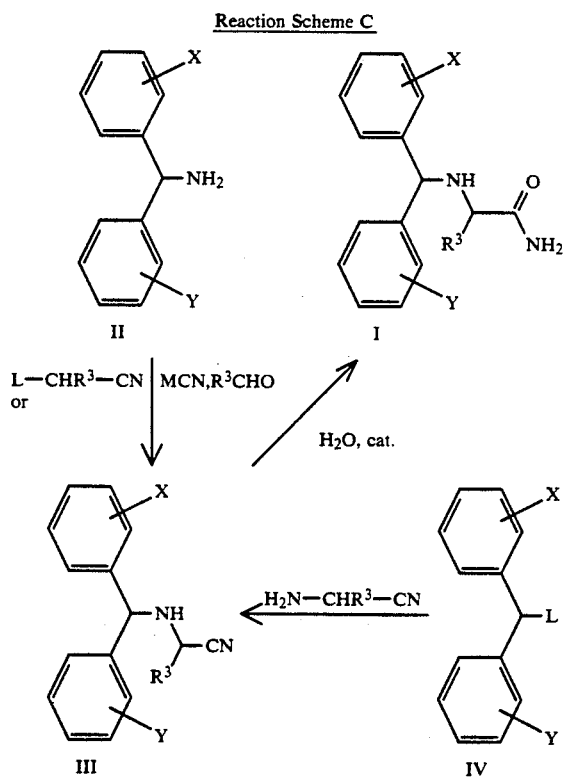

A third method which may be used to synthesize compounds of Formula I, as shown in Reaction Scheme C, involves using a precursor of an amide such as an acid, an ester or a nitrile, Amine II, in the presence of MCN where M stands for a metallic cation or other suitable cation such as a quaternary ammonium or phosphonium cation, is reacted with an aldehyde of the formula $R^3CHO$. This reaction is best conducted in water or if solubility is a problem, the reaction can be conducted in acetonitrile in the presence of aluminum oxide under ultrasound irradiation.

In a variation of Reaction Scheme C, derivative IV can be replaced by the corresponding ketone derivative V, as shown in Reaction Scheme D, which can react with any suitable amino acid derivative under reducing conditions such as a hydrogen atmosphere in the presence of a noble metal catalyst, or in the presence of a reducing agent such as an hydride, particularly a borohydride, to give either I or an analog of III containing the residue of the amino acid derivative involved in the reaction. Table I contains 32 specific compounds within Formula I which can be prepared in accordance with the above-described General Synthetic Procedures:

TABLE 1

| Compound # | Formal Name |
|---|---|
| 1 | 2-[(4-chlorophenyl)phenyl]methylaminoacetamide |
| 2 | 2-[(4-methoxyphenyl)phenyl]methylaminoacetamide |
| 3 | 2-[(4-methylphenyl)phenyl]methylaminoacetamide |
| 4 | 2-[(2-methylphenyl)phenyl]methylaminoacetamide |
| 5 | 2-[(3-methylphenyl)phenyl]methylaminoacetamide |
| 6 | 2-[(3,4-dimethylphenyl)phenyl]methylaminoacetamide |
| 7 | 2-[(4-trifluoromethylphenyl)phenyl]methylaminoacetamide |
| 8 | 2-[di(4-chlorophenyl)]methylaminoacetamide |
| 9 | 2-[(2,5-dimethylphenyl)phenyl]methylaminoacetamide |
| 10 | 2-[(4-bromophenyl)phenyl]methylaminoacetamide |
| 11 | 2-[(4-fluorophenyl)(2-fluorophenyl)]methylaminoacetamide |
| 12 | 2-[(4-fluorophenyl)phenyl]methylaminoacetamide |
| 13 | 2-[di(4-fluorophenyl)]methylaminoacetamide |
| 14 | 2-[(2,4-dimethylphenyl)phenyl]methylaminoacetamide |
| 15 | 2-[(3-chlorophenyl)phenyl]methylaminoacetamide |
| 16 | 2-[(2-chlorophenyl)phenyl]methylaminoacetamide |
| 17 | 2-[(2-chlorophenyl)(4-fluoropheny)]methylaminoacetamide |
| 18 | 2-diphenylmethylaminoacetamide |
| 19 | 2-diphenylmethylaminoacetamide hydrochloride |
| 20 | 2-[(3-fluorophenyl)phenyl]methylaminoacetamide |
| 21 | 2-[(2-fluorophenyl)phenyl]methylaminoacetamide |
| 22 | 2-[di(3-fluorophenyl)]methylaminoacetamide |
| 23 | 2-[di(2-fluorophenyl)]methylaminoacetamide |
| 24 | 2-[(2,4-difluorophenyl)phenyl]methylaminoacetamide |
| 25 | 2-[(3,5-difluorophenyl)phenyl]methylaminoacetamide |
| 26 | 2-[(3,4-difluorophenyl)phenyl]methylaminoacetamide |
| 27 | 2-[(2,3-difluorophenyl)phenyl]methylaminoacetamide |
| 28 | 2-[(2,5-difluorophenyl)phenyl]methylaminoacetamide |
| 29 | 2-[(2,6-difluorophenyl)phenyl]methylaminoacetamide |
| 30 | 2-[(2,4,6-trifluorophenyl)phenyl]methylaminoacetamide |
| 31 | 2-[(2,3,4-trifluorophenyl)phenyl]methylaminoacetamide |
| 32 | 2-[(2,3,4,5,6-pentafluorophenyl)phenyl]methylaminoacetamide |

The following Examples I–VIII are detailed descriptions of the methods of preparation of compounds of Formula I, particularly those listed in Table I. These detailed preparations fall within the scope of, and serve to exemplify, the above described General Synthetic Procedures which form part of the invention. These Examples I–VIII are presented for illustrative purposes only and are not intended as a restriction on the scope of the invention. All parts are by weight unless otherwise indicated.

EXAMPLE I
2-[(4-Chlorophenyl)phenyl]methylaminoacetamide [Compound #1]

A reaction vessel was charged with 7.62 g (30 mmole) of [(4-chlorophenyl)phenyl]methylamine dissolved in 150 ml of absolute ethanol. A mixture of 2.34 g (25 mmole) of chloracetamide and 5.46 g (5 mmole) of sodium bicarbonate was added to the vessel and the resulting suspension was brought to reflux and held at reflux for 2 days. The solution was then cooled, filtered and evaporated under reduced pressure. The residue was dissolved in water and extracted with dichloromethane. The organic phase was dried over magnesium sulfate and evaporated under reduced pressure. The oily residue was solidified in pentane and crystallized in toluene.

| Elementary Analysis: | C | H | N |
|---|---|---|---|
| calc. | 65.57 | 5.50 | 10.16 |
| found | 65.52 | 5.58 | 10.16 |

EXAMPLE II
2-[(4-Methoxyphenyl)phenyl]methylaminoacetamide [Compound #2]

A reaction vessel was charged with 800 mg (3.8 mmole) of [(4-methoxyphenyl)phenyl]methylamine dissolved in 30 ml of absolute ethanol together with 340 mg (3.7 mmole) of chloracetamide and 330 mg (4 mmole) of sodium bicarbonate. The suspension was brought to reflux and held at reflux for 3 days. Solvent was evaporated and the residue was dissolved in dichloromethane and water. The organic phase was dried over potasium carbonate and the solvent evaporated under reduced pressure. The oil obtained was solidified by stirring in an ether pentane mixture. The solid was crystallized in cyclohexane with a few drops of ethyl acetate.

| Elementary analysis: | C | H | N |
|---|---|---|---|
| calc. | 71.09 | 6.71 | 10.36 |
| found | 71.01 | 6.97 | 10.28 |

EXAMPLE III
2-[(3,4-Dimethylphenyl)phenyl]methylaminoacetamide [Compound #6]

A reaction vessel was charged with 11.5 g (54.5 mmole) of [(3,4-dimethylphenyl)phenyl]methylamine dissolved in 200 ml of absolute ethanol. A mixture of 5.05 g (54 mmole) of chloracetamide and 4.62 g (55 mmole) of sodium bicarbonate was added to the reaction vessel and the solution was brought to refulux and held at reflux for 42 hours. Solvent was evaporated under reduced pressure and the residue was diluted with water. The aqueous phase was extracted with dichloromethane and the organic solution dried over potassium carbonate. After evaporation of solvent under reduced pressure, the solid residue was crystallized in ethyl acetate.

| Elementary analysis: | C | H | N |
|---|---|---|---|
| calc. | 76.09 | 7.51 | 10.44 |
| found | 76.13 | 7.60 | 10.57 |

EXAMPLE IV
2-[(4-Trifluoromethylphenyl)phenyl]methylaminoacetamide [Compound #7]

A reaction vessel was charged with 6.7 g (26.7 mmole) of [(3,4-trifluoromethylphenyl)phenyl]methylamine, 4.93 g (26.7 mmole) of iodoacetamide, and 2.24 g (26.7 mmole) of sodium bicarbonate and 200 ml of absolute ethanol. The resulting suspension was brought to reflux and held at reflux for one day. Solvent was evaporated under reduced pressure and the residue was dissolved in water and then extracted with dichloromethane. The organic phase was dried over magnesium sulfate and evaporated under reduced pressure. The oil was solidifed in hexane and crystallized twice in toluene.

| Elementary analysis: | C | H | N |
|---|---|---|---|
| calc. | 62.33 | 4.90 | 9.09 |
| found | 62.07 | 4.93 | 9.12 |

EXAMPLE V
2-[(Bromophenyl)phenyl]methylaminoacetamide [Compound #10]

A reaction vessel was charged with 2.8 g (9.4 mmole) of 2-[(4-bromophenyl)phenyl]methylamine, 1.75 g (9.4 mmole) of iodoacetamide, 1.6 g (1.9 mmole) of sodium bicarbonate and 100 ml of absolute ethanol. The resulting suspension was brought to reflux and held at reflux for 20 hours. Solvent was evaporated under reduced pressure and the residue was diluted with dichloromethane. The organic phase was washed with water, dried over potassium carbonate and evaporated. The white solid was crystallized in isopropanol.

| Elementary analysis: | C | H | N |
|---|---|---|---|
| calc. | 56.44 | 4.74 | 8.78 |
| found | 56.39 | 4.76 | 8.76 |

EXAMPLE VI
2-[(3-Chlorophenyl)phenyl]methylaminoacetamide [Compound #15]

A reaction vessel was charged with 8.8 g (40 mmole) of [(3-chlorophenyl)phenyl]methylamine, 4.2 g (50 mmole) of sodium bicarbonate, 7.4 g (40 mmole) of iodoacetamide and 200 ml of absolute ethanol. The resulting suspension was brought to reflux and held at reflux for 18 hours. Solvent was evaporated and the residue was dissolved in dichloromethane. The organic phase was washed with water, dried over potassium carbonate and evaporated. The oil was dissolved in a minimum of ethanol, to which was added a solution of chlorhydric acid in ether. An oil was decanted which crystallized upon stirring. The white solid was then precipitated from ethanol by addition of ether.

| Elementary analysis: | C | H | N |
|---|---|---|---|
| calc. | 57.89 | 5.18 | 9.00 |
| found | 57.84 | 5.30 | 8.88 |

EXAMPLE VII
2-[(2-Chlorophenyl)-4-fluorophenyl]methylaminoacetamide [Compound #17]

A reaction vessel was charged with 5 g (18.4 mmole) of [(2-chlorophenyl)-4-fluorophenyl]methylamine hydrochloride, 3.4 g (18.4 mmole) of iodoacetamide, 3.2 g (3.8 mmole) of sodium bicarbonate and 150 ml of absolute ethanol. The resulting suspension was brought to reflux and held at reflux for 42 hours. Solvent was evaporated under reduced pressure and the residue was dissolved in water. The aqueous phase was extracted with dichloromethane, and then the organic phase was dried over potassium bicarbonate and evaporated under reduced pressure. The brown oil was solidified in a mixture of ethyl acetate and pentane, and then crystallized twice in a mixture of ethyl acetate and pentane.

| Elementary analysis: | C | H | N |
|---|---|---|---|
| calc. | 61.54 | 4.82 | 9.57 |
| found | 61.46 | 4.81 | 9.52 |

EXAMPLE VIII 2-diphenylmethylaminoacetamide [Compound #18]

A reaction vessel was charged with 18.3 g (100 mmole) of diphenylmethylamine dissolved in 250 ml of ethanol. Then a mixture of 9.35 g (100 mmole) of chloroacetamide and 8.4 g (100 mmole) of sodium bicarbonate was added and the suspension was brought to reflux and held at reflux for 3 days. Solvent was evaporated under reduced pressure and the residue was dissolved in dichloromethane. The organic phase was washed with water, dried over potassium carbonate and solvent was evaporated. The resulting solid crystallized from a mixture of benzene and cyclohexane.

| Elementary analysis: | C | H | N |
|---|---|---|---|
| calc. | 74.97 | 6.71 | 11.65 |
| found | 75.06 | 6.78 | 11.69 |

Table II contains 19 specific compounds which have been synthesized in accordance with the procedures described in Examples I–VIII:

TABLE II

| Compound # | X | Y | $R^1$ | $R^2$ | $R^3$ | Crystallization Solvents | *M.P. °C. |
|---|---|---|---|---|---|---|---|
| 1 | 4-Cl | H | H | H | H | toluene | 127 |
| 2 | 4-OCH$_3$ | H | H | H | H | cyclohexane | 109 |
| 3 | 4-CH$_3$ | H | H | H | H | ethyl acetate | 139 |
| 4 | 2-CH$_3$ | H | H | H | H | ethyl acetate-hexane | 109.5 |
| 5 | 3-CH$_3$ | H | H | H | H | cyclohexane | 79 |
| 6 | 3,4-(CH$_3$)$_2$ | H | H | H | H | ethyl acetate | 143 |
| 7 | 4-CF$_3$ | H | H | H | H | toluene | 101 |
| 8 | 4-Cl | 4-Cl | H | H | H | ethyl acetate-isopropanol | 208** |
| 9 | 2,5(CH$_3$)$_2$ | H | H | H | H | ethyl acetate-isopropanol | 229** |
| 10 | 4-Br | H | H | H | H | isopropanol | 146 |
| 11 | 4-F | 2-F | H | H | H | ethyl acetate-hexane | 69 |
| 12 | 4-F | H | H | H | H | ethyl acetate-hexane | 97 |
| 13 | 4-F | 4-F | H | H | H | ethyl acetate | 90.5 |
| 14 | 2,4-(CH$_3$)$_2$ | H | H | H | H | isopropanol | 128 |
| 15 | 3-Cl | H | H | H | H | ethanol-ether | 199** |
| 16 | 2-Cl | H | H | H | H | ethyl acetate-hexane | 102 |
| 17 | 2-Cl | 4-F | H | H | H | ethyl acetate-hexane | 92 |
| 18 | H | H | H | H | H | benzene-cyclohexane | 116 |
| 19 | H | H | H | H | H | ethanol-ether | 213** |

*M.P. = Melting Point
**Hydrochloride Salt

BIOLOGICAL EVALUATION

Treatment of a mammal afflicted by or susceptible to certain CNS disorders is accomplished by administration of a therapeutically-effective amount of a compound of Formula I. In particular, Compounds #1–19 of Tables I and II were evaluated by in vitro and in vivo animal model assays to determine the pharmacological properties of such compounds and their likely suitability for use as therapeutic drugs in humans. These biological assays, as described below, consisted of prevention of induced convulsions in mice, determination of acute toxicity in mice and animal behavior assays. Except as otherwise specified, the animals used in the in vivo tests were male Swiss albino mice weight 22 to 33 g [CD1, Charles River, France], housed in groups of 10 on a 12-hour dark-light cycle for at least one week before use and fasted overnight prior to testing.

Convulsant-Agent Induced Convulsions

Compounds of Formula I were evaluated as inhibitors of convulsions and death induced by different convulsant agents: 3-mercaptopropionic acid (3-MPA; 120 mg/kg subcutaneously), pentylenetetrazole (PTZ, 55 mg/kg intravenously) and supramaximal electroconvulsive shocks (ECS evoked by a current intensity of 48 mA, 50 Hz. 0.2 sec duration, 10 msec square pulse, corneal electrodes) [W. van Dorsser, D. Barris, A. Cordi and J. Roba, *Arch. Int. Pharmacodyn.*, 266, 239–249 (1983)]. The compounds of the invention were administered orally at a dosage of either 100 mg/kg or 30 mg/kg in a volume of 10 ml/kg each to 5 mice at intervals of 30 minutes or 2 hours before convulsions were induced. The number of mice protected against tonic convulsions and the number of dead mice were noted. Results are given in Table III as a score which represents the total number of mice protected for two groups of 5 animals (3-MPA).

TABLE III

| | Number of Mice Protected From 3-MPA-Induced Convulsions | | | |
|---|---|---|---|---|
| Compound # | Interval: Dose: | 30 min 30 mpk | 30 min 100 mpk | 2 hr 100 mpk |
| 1 | | | 9 | |
| 2 | | | 8 | |
| 3 | | 1 | | |
| 4 | | 5 | | |

TABLE III-continued

| Compound # | Number of Mice Protected From 3-MPA-Induced Convulsions | | |
|---|---|---|---|
| Interval: Dose: | 30 min 30 mpk | 30 min 100 mpk | 2 hr 100 mpk |
| 5 | 2 | | |
| 6 | 2 | | |
| 7 | 4 | | |
| 8 | 1 | | |
| 9 | 1 | | |
| 10 | 3 | | |
| 11 | 8 | | |
| 12 | 9 | 10 | |
| 13 | 5 | | |
| 14 | 3 | 6 | |
| 15 | | 9 | |
| 16 | | 9 | |
| 17 | | 10 | |
| 18 | 9 | 10 | 10 |

Acute Toxicity

The acute toxicity of compounds of the invention was determined after oral administration of the test compound to mice. Compound to be tested was suspended in a 1% tragacanth gum mucilage, and was administered by means of an intragastric probe to a group of three male mice, which doses varied from 3,000 mg/kg down to about 3 mg/kg. Doses used in the test were determined by observing toxic effects on the mice. The mortality was recorded over a period of 15 days. The $LD_{50}$ results reported in Table V were calculated according to published methods [Lichtfield and Wilcoxon, *J. Pharmacol. Exp. Ther.*, 96, 99 (1949)] and expressed in mg or test compound per kilogram of mouse body weight.

Behavioral Studies

Behavioral effects of compounds of the invention on animals were determined by observations taken at 5 to 6 hours and at 24 hours after administration of compounds in the acute toxicity studies. Determinations were made based on a method derived from that of S. Irwin [See R. A. Turner, *Screening Methods in Pharmacology*, Chapter 3, pages 22-34, Academic Press, N.Y. (1965)]. If an anomaly were noted, the observation was extended and smaller doses were tested. Possible types of behavior to be observed are as follows: analgesia (AAG), convulsions (CON), depression (DEP), exophthalmia (EOP), excitation (EXC), hyperalgesia (HAG), hypothermia (ATH), hypotonia (ATN), piloerection (PIE), palpebral ptosis (PTO), reduction of the pinna reflex (RPI), reduction of the rearing reflex (RRE), reduction of the flexion reflex (RRF), sedation (SED), tremors (TRE), cyanosis (CYA), diarrhea (DIA), increase of the pinna reflex (HPI), increase of the flexion reflex (HRF), dyspnea (DYS). Behaviors observed are reported in Table IV by numbers which represent the dose at which the behavior is observed.

TABLE IV

| Compound # | $LD_{50}$ (mg/kg) | Behavior (mg/kg) |
|---|---|---|
| 1 | 2400 | 1000:SED,ATN, CON |
| 2 | | |
| 3 | >3000 | 1000:SED 3000:DEP |
| 4 | 780 | 300:SED,ATN |
| 5 | 3500 | 1000:SED |
| 6 | 3500 | 3000:SED,ATN |
| 7 | | |
| 8 | | |
| 9 | | |
| 10 | >1000 | 1000:SED, |
| 11 | 315 | 100:SED 1000:DEP,CON |
| 12 | | |
| 13 | | |
| 14 | | |
| 15 | | |
| 16 | | |
| 17 | | |
| 18 | 1025 | 1000:DEP,PTO |

Based upon data generated from the previously-described anti-convulsant experiments, $ED_{50}$ values were calculated at which Compound #18 inhibits convulsions induced by the convulsant agents listed in Table V.

TABLE V

| Convulsant | Inhibition of Convulsions by Cpd. #18 ($ED_{50}$;mg/kg) |
|---|---|
| 3-MPA | 9.3 |
| ECS | 26 |
| PZT | 66 |

Chronic Focal Epilepsy Assay

In a model of chronic focal epilepsy where cobalt powder is placed on rat frontal cortex, the animals develop, after several days, chronic expression of afterdischarge-like spike activity which can be recorded by EEG. Compound #18 was found to have when administered by intraperitoneal route, a threshold dose of 50 mg/kg for inhibiting these spike activities with the effect being observed from 14-90 minutes.

5HTP-Induced Head Twitch

Compound #18 was evaluated for inhibition of head twitches produced in mice by administration of L-5-hydroxytryptophan (5HTP, 10 mg/kg intraperitoneously) after nialamide treatment (50 mg/kg intraperitoneal, 22 hours before the test). The head twitches were counted for 45 min. starting 15 min. after 5HTP administration. [E. Friedmann & al.; *Europ. J. Pharmocol.*, 89, 69-76 (1983)]. Compound #18 was given 2 hours before the 5HTP challenge and has a $ED_{50}$ of 10 mg/kg p.o. Suprisingly, Compound #18 inhibited 5HTP-induced head twitch. This property of Compound #18 is unexpected inasmuch as the compound 2-pentylaminoacetamide potentiates 5HTP-induced head twitch under similar test conditions.

Clonidine-Induced Hypomotility

Given alone, clonidine inhibits spontaneous locomotor and rearing activity. Eight test mice were treated with Compound #18 and subsequently with clonidine (150 mg/kg, intraperitoneal). Then, 90 min. after clonidine administration the mice were placed in a rectangular open field of 47×53 cm, having a floor divided into 36 boxes of about 8×9 cm. The number of boxes through which the animal goes in 3 min. and the number of rearing episodes were noted. A dose of 10 mg/kg of Compound #18 seems unable to alter the hypomotility induced by the $\alpha_2$ agonist clonidine.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. Compound which is 2-[(4-fluorophenyl)phenyl]methylaminoacetamide.

2. Compound which is 2-[(2-chlorophenyl)(4-fluorophenyl)]methylaminoacetamide.

3. Compound which is 2-[(3-fluorophenyl)phenyl]methylaminoacetamide.

4. A pharmaceutical composition comprising a therapeutically-effective amount of an active compound and a pharmaceutically-acceptable carrier or diluent, said active compound selected from the group consisting of 2-[(4-fluorophenyl)phenyl]methylaminoacetamide;
2-[(2-chlorophenyl)(4-fluorophenyl)]methylaminoacetamide;
2-[(3-fluorophenyl)phenyl]methylaminoacetamide.

5. A method for treating a mammal afflicted with or susceptible to epilepsy, convulsions, depression, dyskinesia or a cognitive disorder, said method comprising administering a therapeutically-effective amount of a compound selected from the group consisting of 2-[(4-fluorophenyl)phenyl]methylaminoacetamide;
2-[(2-chlorophenyl)(4-fluorophenyl)]methylaminoacetamide;
2-diphenylmethylaminoacetamide hydrochloride; or
2-[(3-fluorophenyl)phenyl]methylaminoacetamide.

* * * * *